(12) United States Patent
Saito et al.

(10) Patent No.: US 9,981,125 B2
(45) Date of Patent: May 29, 2018

(54) COSMETIC DEVICE, METHOD OF APPLYING CURRENT, AND STORAGE MEDIUM

(71) Applicant: SHISEIDO COMPANY, LTD., Tokyo (JP)

(72) Inventors: Naoki Saito, Kanagawa (JP); Yuichiro Mori, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 476 days.

(21) Appl. No.: 14/430,977

(22) PCT Filed: Sep. 24, 2013

(86) PCT No.: PCT/JP2013/075730
§ 371 (c)(1),
(2) Date: Mar. 25, 2015

(87) PCT Pub. No.: WO2014/054459
PCT Pub. Date: Apr. 10, 2014

(65) Prior Publication Data
US 2015/0246227 A1    Sep. 3, 2015

(30) Foreign Application Priority Data
Oct. 5, 2012    (JP) ................................. 2012-223698

(51) Int. Cl.
*A61N 1/30*    (2006.01)
*A61N 1/32*    (2006.01)

(52) U.S. Cl.
CPC ................... *A61N 1/325* (2013.01)

(58) Field of Classification Search
CPC ......... A61N 1/30; A61N 1/325; A61N 1/0428
(Continued)

(56) References Cited

U.S. PATENT DOCUMENTS 3,885,573 A * 5/1975 Hara ..................... A61N 1/40
607/68
4,226,246 A * 10/1980 Fragnet ................ A61N 1/0408
607/66

(Continued)

FOREIGN PATENT DOCUMENTS

AU    2003271179    4/2005
CN    102395403    3/2012

(Continued)

OTHER PUBLICATIONS

Taiwanese Office Action dated Jan. 20, 2017.
Chinese Office Action dated Nov. 11, 2015.
International Search Report dated Jan. 7, 2014.

*Primary Examiner* — Nathan R Price
*Assistant Examiner* — Gerald Landry, II
(74) *Attorney, Agent, or Firm* — IPUSA, PLLC (57) ABSTRACT

A cosmetic device 10 for performing iontophoresis on the skin 40 of a human, includes carbon sheet electrodes 33A and 33B to be mounted on the skin 40 of the human, and provides an electric signal to the carbon sheet electrodes 33A and 33B, the electric signal being obtained by superimposing an AC signal and a high-frequency signal that has a frequency higher than a frequency of the AC signal while setting a position to which the high-frequency signal is superimposed at a polar region of the AC signal that does not contribute to the iontophoresis.

11 Claims, 6 Drawing Sheets

(58) Field of Classification Search
USPC ....... 424/449; 600/372, 393; 604/20; 607/46
See application file for complete search history.

(56) References Cited

U.S. PATENT DOCUMENTS

| | | | | |
|---|---|---|---|---|
| 4,456,012 | A * | 6/1984 | Lattin | A61N 1/08 604/20 |
| 5,931,859 | A * | 8/1999 | Burke | A61N 1/322 132/317 |
| 6,029,090 | A * | 2/2000 | Herbst | A61N 1/0412 607/66 |
| 6,148,232 | A * | 11/2000 | Avrahami | A61N 1/30 600/372 |
| 6,684,106 | B2 * | 1/2004 | Herbst | A61N 1/0412 607/66 |
| 6,708,060 | B1 * | 3/2004 | Avrahami | A61N 1/30 600/372 |
| 6,801,804 | B2 * | 10/2004 | Miller | A61N 1/08 604/20 |
| 8,190,252 | B2 | 5/2012 | Imran | |
| 8,449,522 | B2 * | 5/2013 | Castel | A61K 8/02 604/501 |
| 2002/0038101 | A1 * | 3/2002 | Avrahami | A61N 1/30 604/20 |
| 2005/0273046 | A1 * | 12/2005 | Kwiatkowski | A61K 9/0009 604/20 |
| 2006/0089590 | A1 * | 4/2006 | Higuchi | A61K 9/0009 604/20 |
| 2008/0046027 | A1 | 2/2008 | Cook et al. | |
| 2008/0063703 | A1 * | 3/2008 | Gross | A61B 1/00156 424/463 |
| 2009/0292328 | A1 * | 11/2009 | Birkill | A61N 1/0428 607/3 |
| 2010/0312166 | A1 * | 12/2010 | Castel | A61K 8/02 604/20 |
| 2011/0082411 | A1 * | 4/2011 | Imran | A61N 1/30 604/20 |
| 2011/0093033 | A1 * | 4/2011 | Nekhendzy | A61N 1/36017 607/46 |
| 2013/0023815 | A1 * | 1/2013 | Imran | A61N 1/0448 604/20 |
| 2013/0218067 | A1 | 8/2013 | Saito et al. | |

FOREIGN PATENT DOCUMENTS

| | | |
|---|---|---|
| JP | 4217984 | 2/2009 |
| JP | 2012-517321 | 8/2012 |
| TW | 201232279 | 8/2012 |
| WO | 2005/035051 | 4/2005 |
| WO | 2012/063883 | 5/2012 |

* cited by examiner

COSMETIC DEVICE, METHOD OF APPLYING CURRENT, AND STORAGE MEDIUM

BACKGROUND OF THE INVENTION

1. Field of the Invention

The present invention relates to a cosmetic device, a method of applying a current and a storage medium for performing iontophoresis.

2. Description of the Related Art

Conventionally, various methods are known by which the skin or the like of a user can be made into an appropriate state by applying a certain signal (a current or the like, for example) to the skin or the like of the user. For example, as an example of cosmetic methods, iontophoresis or the like is known by which an aqueous active ingredient, for example, can be effectively introduced into the skin by flowing a faint current through the skin.

For example, the stratum corneum of the skin has a barrier function to prevent invasion of contaminants. Thus, impregnation of aqueous vitamin C or the like included in skin lotion is prevented by such a barrier function and it is difficult for the aqueous vitamin C or the like to be impregnated into a deep layer of the skin just by coating the skin lotion on the skin. However, according to the above described iontophoresis, using a power of electricity, the active ingredient in the skin lotion can be impregnated into the deep layer of the skin by passing through a barrier layer.

Here, conventionally, a specific cosmetic device for a user to perform the above described cosmetic treatment by herself/himself is known (see Patent Document 1, for example).

PATENT DOCUMENT

[Patent Document 1] Japanese Patent No. 4,217,984

However, the specific cosmetic device or the like as described above in Patent Document 1 is relatively expensive and it is difficult to obtain.

SUMMARY OF THE INVENTION

The present invention is made in light of the above problems, and provides a technique for surely performing iontophoresis by a high-frequency AC signal that is output from an output terminal of a general data processing apparatus.

According to a first aspect, there is provided a cosmetic device for performing iontophoresis on the skin of a human, including: an electrode to be mounted on the skin of the human; and an electric signal providing unit that provides an electric signal to the electrode, the electric signal being obtained by superimposing an AC signal and a high-frequency signal that has a frequency higher than a frequency of the AC signal while setting a position to which the high-frequency signal is superimposed at a polar region of the AC signal that does not contribute to the iontophoresis.

According to a second aspect, there is provided a method of applying a current for performing iontophoresis on the skin of a human, including: providing an electric signal to an electrode that is to be mounted on the skin of the human, the electric signal being obtained by superimposing an AC signal and a high-frequency signal that has a frequency higher than a frequency of the AC signal while setting a position to which the high-frequency signal is superimposed at a polar region of the AC signal that does not contribute to the iontophoresis.

According to a third aspect, there is provided a storage medium that stores an electric signal obtained by superimposing an AC signal and a high-frequency signal that has a frequency higher than a frequency of the AC signal.

According to the embodiment, it is possible to surely perform iontophoresis by a high-frequency AC signal that is output from an output terminal of a general data processing apparatus.

DETAILED DESCRIPTION OF THE PREFERRED EMBODIMENTS

As described above, the specific cosmetic device or the like is relatively expensive and it is difficult to obtain.

Thus, it can be considered that, for substitution of the specific cosmetic device, for example, an electric signal for performing iontophoresis is obtained from a contents output terminal (an earphone terminal, a Dock terminal or a Universal Serial Bus (USB) terminal) of a general data processing apparatus such as a mobile phone, a Personal Computer (PC), a Portable Device (PD), a Personal Data Assistant (PDA), a gaming machine or the like.

However, the specification of the contents output terminals of data processing apparatuses are different between apparatuses. Further, although it is common to use a pulse direct current as an electric signal to be supplied to an electrode for iontophoresis, almost no apparatuses can output a signal of the pulse direct current.

Thus, it can be considered that an AC signal is used as the electric signal to be supplied to the electrode, however, as will be explained below, effects can be obtained only by a low-frequency signal (a signal less than or equal to 1 Hz) in the iontophoresis using the AC signal.

Thus, it is necessary to output a low-frequency signal of less than or equal to 1 Hz from the data processing apparatus. However, an audio signal that is output from the data processing apparatus generally only corresponds to frequencies of an audible range (20 to 20,000 Hz). Thus, a wave form may be unstable when trying to output a low-frequency signal of less than or equal to 1 Hz and it was difficult to stably perform the iontophoresis.

Next, an embodiment is explained with reference to drawings.

Figure 1:
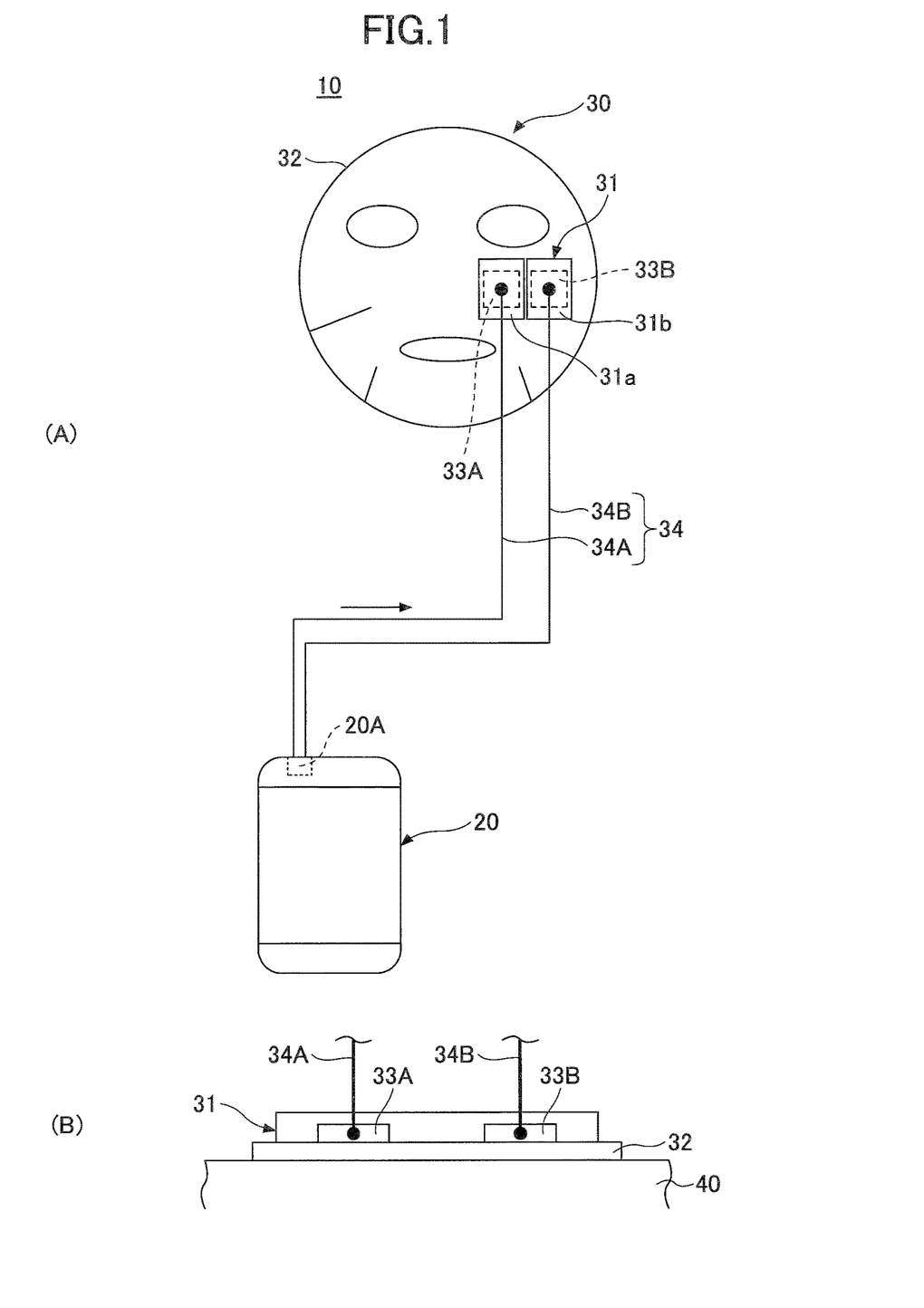
FIG. 1 is a view illustrating a structure of a cosmetic device of an embodiment.

FIG. 1-(A) is a view illustrating an entire structure of a cosmetic device 10 of the embodiment, and FIG. 1-(B) is a cross-sectional view illustrating a structure of an electrode pad 31 that is connected to a data processing apparatus 20.

As illustrated in FIG. 1-(A), the cosmetic device 10 includes the data processing apparatus 20 and a cosmetic treatment device 30.

The data processing apparatus 20 is a multifunctional data terminal apparatus capable of actualizing various functions by incorporating application programs in addition to actualize basic functions such as a telephone function, an Internet connecting function, a music reproducing function or the like, for example.

In this embodiment, the iontophoresis (cosmetic treatment) is performed on a user (a person to be treated) by functioning the data processing apparatus 20 that is the multifunctional data terminal apparatus as a part of the cosmetic device 10 and using an electric signal (referred to as a "signal for iontophoresis") output from the data processing apparatus 20.

For the data processing apparatus 20 of the embodiment, a general data processing apparatus that may be possessed by a user for a purpose other than cosmetics may be used, such as a mobile phone such as an iPhone (registered trademark), a smartphone or the like, a PD such as a PDA, an iPod (registered trademark), an iPad (registered trademark) or the like, a PC or the like. However, this is not limited so in the invention. Here, a specific structure of the data processing apparatus 20 is explained later, for the purpose of explanation.

The cosmetic treatment device 30 includes an electrode pad 31 and an impregnating material 32 that impregnates an active ingredient such as cosmetics, chemical solution or the like (in the following, the skin lotion is exemplified). The electrode pad 31 includes insulating base members 31a and 31b and carbon sheet electrodes 33A and 33B that are provided on the insulating base members 31a and 31b, respectively.

The carbon sheet electrodes 33A and 33B are connected to an output terminal 20A of the data processing apparatus 20 via an audio cable 34. The output terminal 20A may be a terminal corresponding to more than or equal to two polarities. Specifically, one of the output terminals 20A is connected to the carbon sheet electrode 33A via a cable 34A and the other of the output terminals 20A is connected to the carbon sheet electrode 33B via a cable 34B.

Here, for the output terminal 20A, an earphone terminal, a Dock terminal, a Universal Serial Bus (USB) terminal or the like provided in the data processing apparatus 20 may be used.

The impregnating material 32 is made of a water-content material such as cotton, non-woven fabric or the like. The mask 32 is prepared in various embodiments corresponding to sites to which the iontophoresis is to be performed. For the example illustrated in FIG. 1-(A), a mask to mount on a face is exemplified as the impregnating material 32 (hereinafter, the illustrated impregnating material is referred to as the mask 32).

The component of the cosmetics is electrolyte so that the component is ionized to positive ions and negative ions. Thus, even under a state in which the component of the skin lotion is impregnated in the mask 32, the component is ionized to positive ions and negative ions.

When a user performs an iontophoresis treatment using the cosmetic device 10, first, the user mounts the cosmetic treatment device 30 on a desired skin 40 at which the iontophoresis is to be performed.

Specifically, the mask 32 that composes the cosmetic treatment device 30 is mounted on the desired skin 40 at which the iontophoresis is to be performed.

Subsequently, the electrode pad 31 is mounted on the mask 32. The electrode pad 31 includes the carbon sheet electrodes 33A and 33B and each of the carbon sheet electrodes 33A and 33B contacts the mask 32 in which skin lotion is impregnated when being mounted.

The signal for iontophoresis output from the data processing apparatus 20 is provided to the carbon sheet electrode 33A. When the signal for iontophoresis is provided to the carbon sheet electrode 33A, faint current corresponding to the wave form of the signal for iontophoresis flows in the skin via the carbon sheet electrodes 33A and 33B, and the chemical agent included in the skin lotion is promoted to be impregnated in the skin 40 by the charge repulsion due to the current. With this, the iontophoresis can be performed on the skin of the user. Here, the wave form or the like of the signal for iontophoresis is explained in detail later.

Figure 2:
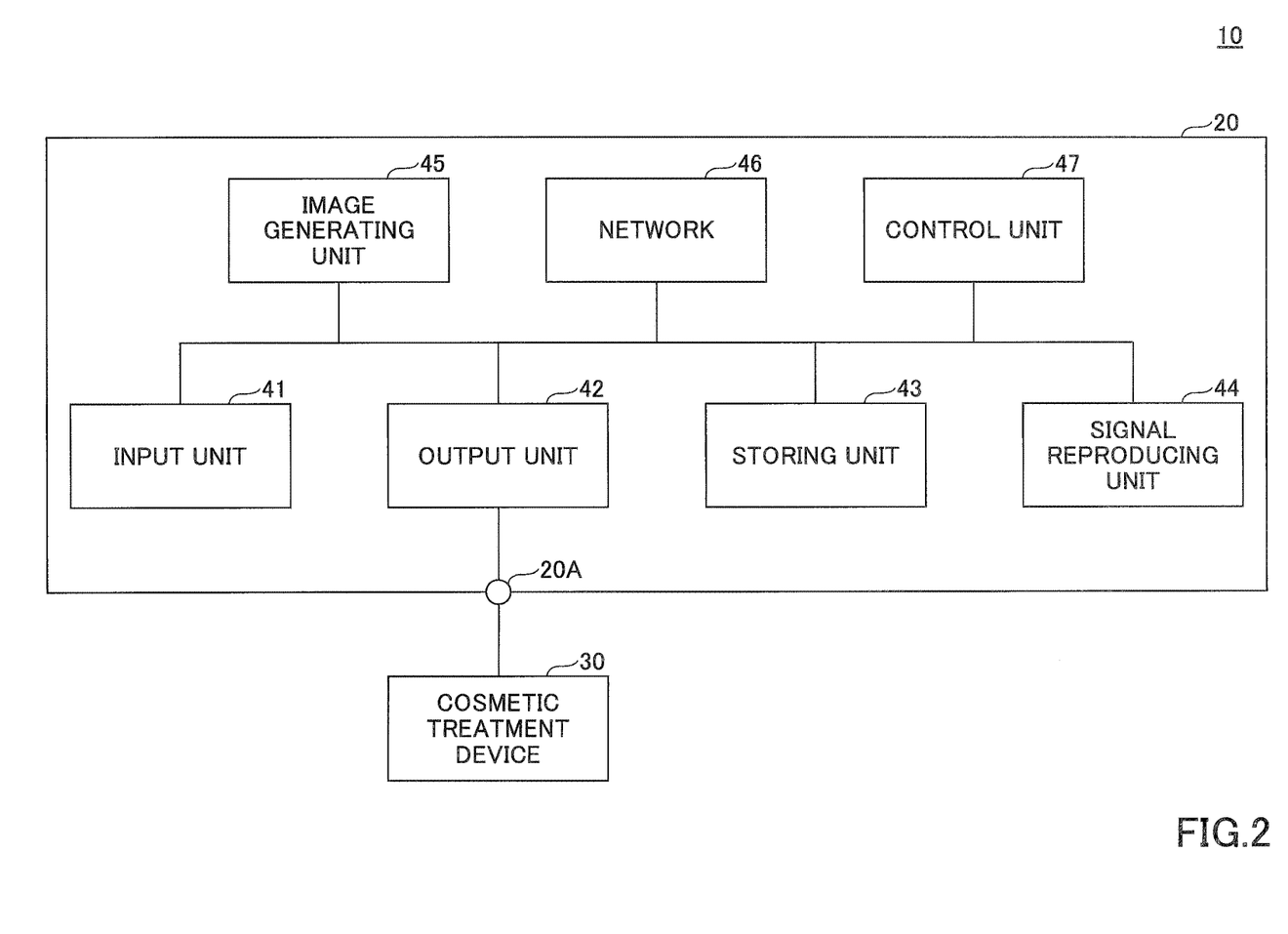
FIG. 2 is a view illustrating a functional structure of the cosmetic device of the embodiment.

Next, a functional structure of the data processing apparatus 20 is explained with reference to FIG. 2.

The data processing apparatus 20 includes an input unit 41, an output unit 42, a storing unit 43, a signal reproducing unit 44, an image generating unit 45, a network connecting unit 46, a control unit 47 and the like.

The input unit 41 is composed by an operation key of a mobile phone, a smartphone or the like, a pointing device such as a keyboard, a mouse or the like of a PC or the like, for example. The input unit 41 accepts an input of starting and ending of various instructions or the like from a user or the like. Further, the input unit 41 may be composed by a sound input terminal such as a microphone or the like, for example.

The output unit 42 is composed of display screens such as a display or the like, for example. The output unit 42 displays a content input by the input unit 41, and a content performed based on the input content. At this time, by using a touch panel, the input unit 41 and the output unit 42 may be integrally formed.

Further, the output terminal 20A for outputting an audio signal or the like is connected to the output unit 42. The above described cosmetic treatment device 30 is connected to the output terminal 20A. Here, the output terminal 20A includes the above described Dock terminal, the USB terminal or the like.

The storing unit 43 stores application programs for having the data processing apparatus 20 perform various processes and various data necessary for the processes. An application program for performing the iontophoresis treatment of the embodiment (hereinafter, referred to as a program for the iontophoresis treatment), the signal for iontophoresis that is reproduced by the signal reproducing unit 44, user data, data of treatment contents such as the iontophoresis or the like, data of treatment period or the like is also stored in the storing unit 43.

The signal reproducing unit 44 reproduces the signal for iontophoresis stored in the storing unit 43, and outputs it to the cosmetic treatment device 30 via the output unit 42 and the output terminal 20A. The signal for iontophoresis is stored in the storing unit 43 in a form of an audio file format such as a wav (WAVE) file, AIFF, mp3, mp4, WMA, AAC, RealAudio, MIDI or the like, or a movie file such as AVI, Quick Time, Mpeg-1, Mpeg-2, WMV, FLV or the like, for example.

Hereinafter, a general name of a file format capable of being used as a file for the signal for iontophoresis is referred to as a "contents file". Thus, the contents file includes an audio file and a movie file. Further, the contents file includes various files that are convertible to a file format capable of being regenerated by the signal reproducing unit 44 by performing file conversion. Further, in the following explanation, a contents file in which the signal for iontophoresis is recorded is specifically referred to as a "file of the signal for iontophoresis".

The image generating unit 45 generates a menu screen for having a user input a treatment content, screens for displaying a treatment content, a treatment process, a treatment result or the like. The screens generated by the image generating unit 45 are displayed on a display or the like that composes the output unit 42.

The network connecting unit 46 is configured to be capable of being connected to a communication network such as the Internet or the like, for example. Thus, the data processing apparatus 20 is capable of installing the various programs and the various data (including the program for the iontophoresis treatment and the file of the signal for iontophoresis) that are performed in the data processing apparatus 20 via the network connecting unit 46.

The various programs and the various data installed via the network connecting unit 46 are stored in the storing unit 43. Further, various data (data regarding the iontophoresis, for example) generated in the data processing apparatus 20 may be sent to an external apparatus (a server or the like of a cosmetic maker that delivers the iontophoresis program, for example) via the communication network.

By executing the various programs stored in the storing unit 43, the control unit 47 actualizes functions corresponding to the programs, respectively. In this embodiment, by executing the program for the iontophoresis treatment stored in the storing unit 43, the control unit 47 has the data processing apparatus 20 function as the cosmetic device 10.

Specifically, by executing the program for the iontophoresis treatment, the control unit 47 generates a signal for iontophoresis by reproducing the file of the signal for iontophoresis stored in the storing unit 43 by the signal reproducing unit 44 and provides it to the cosmetic treatment device 30 via the output unit 42 and the output terminal 20A. Further, the cosmetic treatment device 30 may include a device protecting unit that prevents troubles such as overcurrent to the output terminal 20A, in addition to the above described units.

Here, the output terminal 20A, the output unit 42, the storing unit 43, the signal generating unit 44 and the control unit 47 compose an electric signal providing unit of claims.

Figure 3:
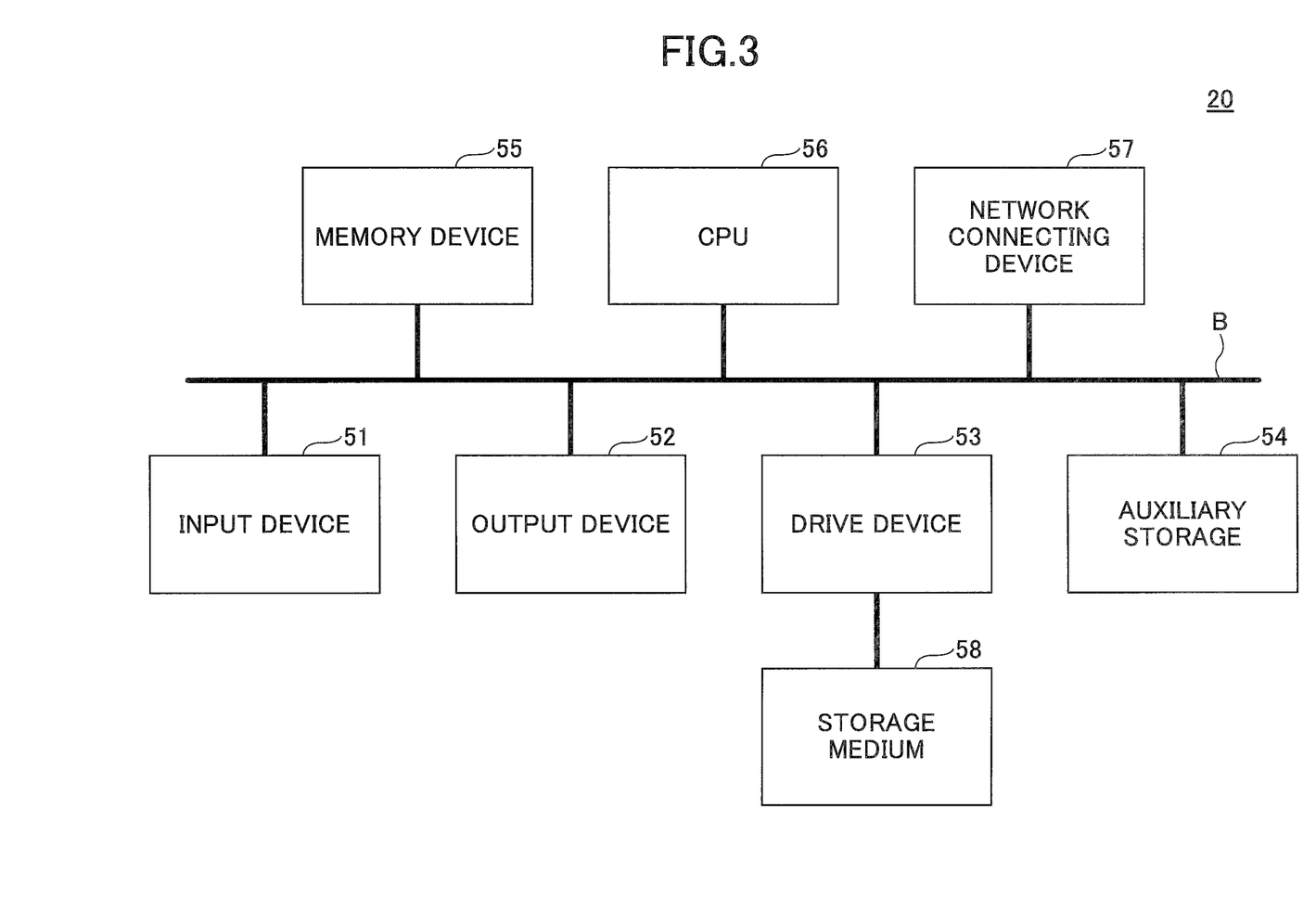
FIG. 3 is a view illustrating a hardware structure of the cosmetic device of the embodiment.

Next, with reference to FIG. 3, a hardware structure of the data processing apparatus 20 is explained. FIG. 3 is a view illustrating an example of a hardware structure actualizing a data processing unit.

As illustrated in FIG. 3, the data processing apparatus 20 includes an input device 51, an output device 52, a drive device 53, an auxiliary storage 54, a memory device 55, a central processing unit (CPU) 56, a network connecting device 57, a storage medium 58 and the like, and each of them are connected by a bus B with each other.

The input device 51 is composed by a keyboard operated by a user, a pointing device such as a mouse or the like, a touch panel operated by a user or the like, and is used to input various operational instructions from the user.

The output device 52 includes a display or the like for displaying various windows, data or the like necessary for the user to operate the data processing apparatus 20. Further, the output unit 52 includes the output terminal 20A (an earphone terminal, a Dock terminal, an USB terminal or the like) for outputting sound to a speaker, an earphone or the like.

The storage medium 58 is attached to the drive device 53 and the drive device 53 reads various programs and various data stored in the storage medium 58. The various programs and the various data read by the drive device 53 are stored in the auxiliary storage 54.

Here, for the storage medium 58 that stores various programs and various data, various types of storage media may be used such as a storage medium that optically, electrically or magnetically stores data such as a CD-ROM, a flexible disk, a magneto-optical disk (MO) or the like, a semiconductor memory that electrically stores data such as a ROM, a flash memory or the like, or the like.

The auxiliary storage 54 is a storage unit such as a hard disk or the like. The auxiliary storage 54 inputs and outputs various files or various data to and from the CPU 56 in accordance with processes of various programs executed by the CPU 56.

The memory device 55 stores an execution program or the like that is read out by the CPU 56 from the auxiliary storage 54. Here, the memory device 55 may be composed of a ROM, a RAM or the like.

The CPU 56 executes various arithmetic processes, input and output processes of data between each hardware structure unit, control processes of the entirety of the computer or the like based on a control program such as an OS or the like and an execution program stored in the memory device 55.

The network connecting device 57 actualizes the above described network connecting unit 46, and is configured to be capable of being connected to a communication network such as the Internet or the like.

According to the cosmetic device 10 of the embodiment, the data processing apparatus 20 having the above described hardware structure is used. This data processing apparatus 20 does not include a hardware structure that is specifically added in order to perform the iontophoresis treatment. Thus, for the data processing apparatus 20, a multifunctional data terminal apparatus that is generally commercially available one can be used as it is.

In this embodiment, the processing apparatus 20 and the cosmetic treatment device 30 are made to function as the cosmetic device 10 capable of performing the iontophoresis treatment by installing a program for the iontophoresis treatment and a file of the signal for iontophoresis in the data processing apparatus 20 and connecting the cosmetic treatment device 30 to the data processing apparatus 20.

The program for the iontophoresis treatment and the file of the signal for iontophoresis that are installed in the data processing apparatus 20 may be installed, if there is a providing server that provides these program and file, from the providing server via the communication network, or may be installed, if provided by being recorded on the storage medium 58 such as a CD-ROM or the like, by reading the storage medium 58 by the drive device 53. Further, these may be pre-installed when manufacturing the data processing apparatus 20.

Figure 4:
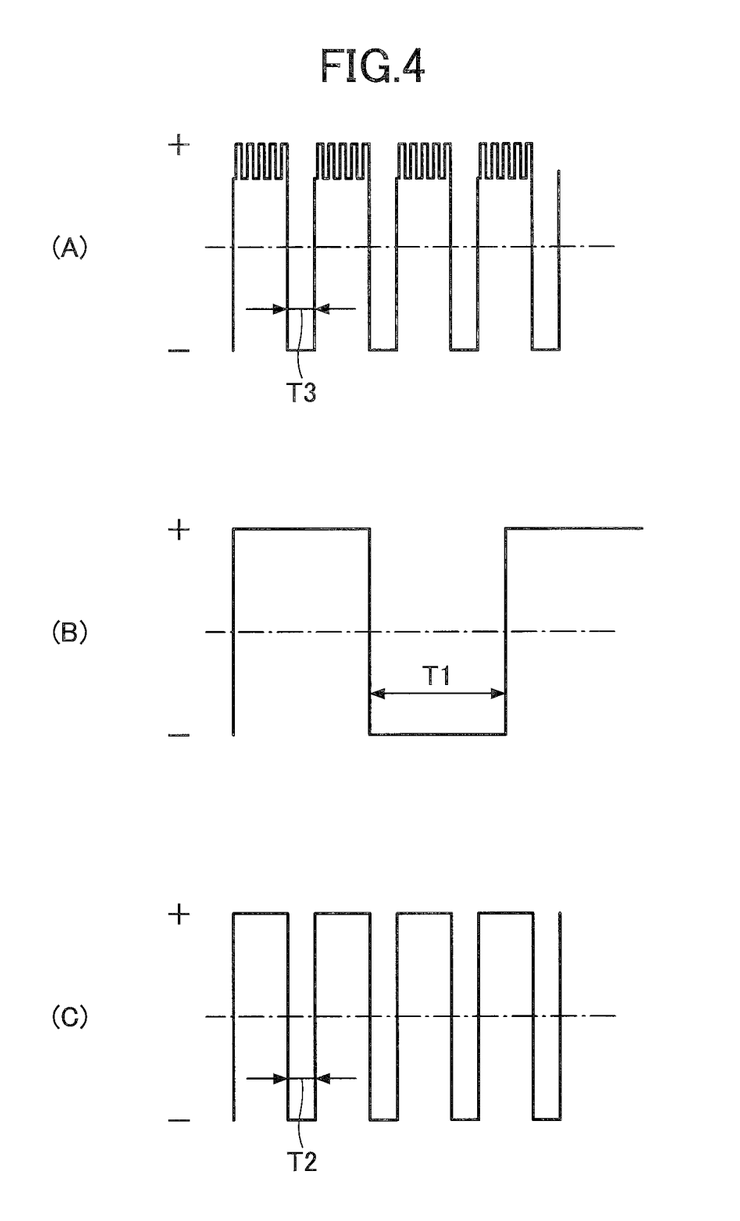
FIG. 4 is a view illustrating a wave form of a signal for iontophoresis that is used when performing iontophoresis by the cosmetic device of the embodiment, with a wave form of reference examples.

FIG. 4-(A) illustrates a signal wave form of the signal for iontophoresis of the embodiment. On the other hand, FIG. 4-(B) illustrates a signal wave form of a signal for iontophoresis of a first reference example, and FIG. 4-(C) illustrates a signal wave form of a signal for iontophoresis of a second reference example.

As described above, the active ingredient such as cosmetics, chemical solution or the like is electrolyte, and when performing the iontophoresis on the skin of a human, depending on its kind, one of polar regions, positive (+) and negative (−), of an AC pulse signal contributes to the iontophoresis while the other of the polar regions does not contribute to the iontophoresis. In this embodiment, the explanation is made assuming that the negative (−) polar region contributes to the iontophoresis.

First, the signal for iontophoresis of first reference example illustrated FIG. 4-(B) is explained. The signal for iontophoresis of the first reference example is a low-frequency AC pulse signal whose signal frequency is less than or equal to 1 Hz. The signal for iontophoresis of the first reference example is one that has been conventionally used as a signal for iontophoresis.

When such a low-frequency AC pulse signal whose frequency is less than or equal to 1 Hz is used for the signal for iontophoresis, the period is long so that the time period for each of the positive (+) polar regions and the negative (−) polar regions of the AC pulse signal becomes long. This means that the time period T1 for each negative (−) polar region that contributes to the iontophoresis becomes long in the signal for iontophoresis. Thus, the active ingredient can move inside of the skin, easily impregnated inside of the skin, and the iontophoresis can be preferably performed. Here, in the following, the time period for the region that contributes to the iontophoresis in the signal for iontophoresis is referred to as an "iontophoresis contribution time period".

However, the output terminal 20A of the multifunctional data terminal apparatus, that is the data processing apparatus 20, does not correspond to a low-frequency signal whose frequency is less than or equal to 1 Hz, and thus, as described above, it is difficult to provide such a low-frequency signal for iontophoresis from the data processing apparatus 20 to the cosmetic treatment device 30.

The signal for iontophoresis of the second reference example illustrated in FIG. 4-(C) has a frequency larger than 1 Hz in an audible range about 20 to 20,000 Hz, for example. Thus, the signal for iontophoresis illustrated in FIG. 4-(C) has a frequency higher than the frequency illustrated in FIG. 4-(B) that is generally used as the iontophoresis signal.

When the AC pulse signal whose frequency is larger than 1 Hz is used as the signal for iontophoresis, the time period T2 for the region that contributes to the iontophoresis (iontophoresis contribution time period) of the signal for iontophoresis is shorter than the iontophoresis contribution time period T1 illustrated in FIG. 4-(B) (T2<T1). Thus, even when the active ingredient moves toward inside the skin during the iontophoresis contribution time period T2 in which the AC pulse signal of the negative (−) polar region is applied, for example, the AC pulse signal of the positive (+) polar region, that is the opposite polar, is applied before the active ingredient is impregnated inside the skin and the active ingredient moves in a direction opposite to the inside of the skin.

Thus, when the iontophoresis treatment is performed using the signal for iontophoresis whose frequency is larger than 1 Hz, as the iontophoresis contribution time period T2 is short, the efficiency of the iontophoresis is reduced compared with a case when the signal for iontophoresis as illustrated in FIG. 4-(B) is used.

Figure 5:
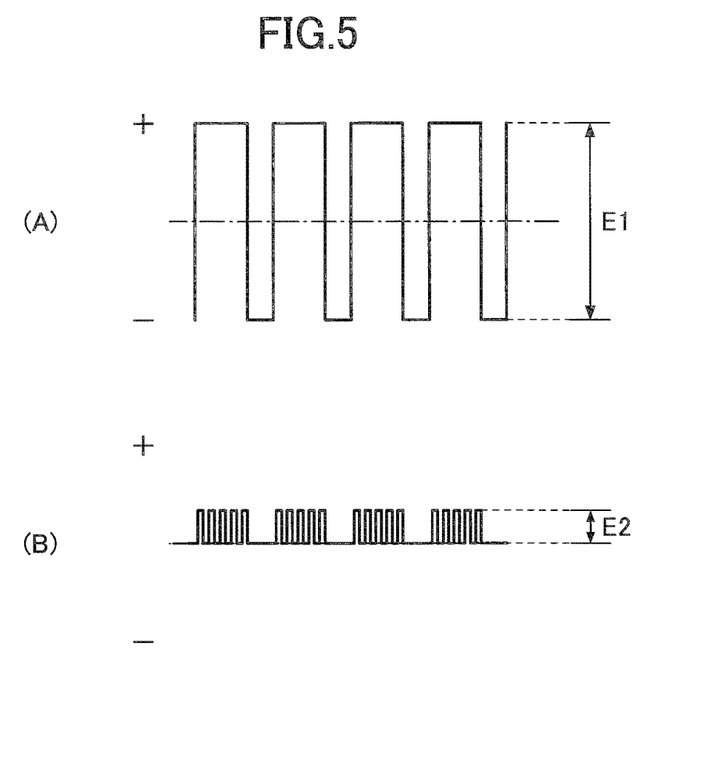
FIG. 5 is a view illustrating an AC signal and a high-frequency signal that compose the signal for iontophoresis that is used when performing the iontophoresis by the cosmetic device of the embodiment.

On the other hand, as illustrated in FIG. 4-(A), the signal for iontophoresis of the embodiment has a signal wave form in which a high-frequency signal whose frequency is higher than that of the AC pulse signal is superimposed at a polar region (a positive polarity region in this embodiment) of the AC pulse signal that does not contribute to the iontophoresis. The signal for iontophoresis of the embodiment illustrated in FIG. 4-(A) has a structure in which the high-frequency signal, that is the noise signal, is superimposed on the polar region of the signal for iontophoresis illustrated in FIG. 4-(C) that does not contribute to the iontophoresis. FIG. 5 is a view separately illustrating the AC pulse signal and the high-frequency signal that compose the signal for iontophoresis of the embodiment.

FIG. 5-(A) illustrates the AC pulse signal. The AC pulse signal illustrated in FIG. 5-(A) is an AC signal that can be output from the general data processing apparatus and having a frequency whose lower limit value is more than 1 Hz and whose upper limit is audible frequency, for example. Specifically, the frequency of the AC pulse signal is an AC signal whose frequency f is within a range of $1\ Hz<f\leq20{,}000\ Hz$. By selecting the frequency f of the AC pulse signal within such a range, it is possible to provide the signal for iontophoresis of the embodiment from the output terminal 20A of the data processing apparatus 20 to the cosmetic treatment device 30.

FIG. 5-(B) illustrates a high-frequency signal that is superimposed on the AC pulse signal. The high-frequency signal may be a burst direct current pulse signal. The frequency of the high-frequency signal may be greater than or equal to 5 times and less than or equal to 20 times of the frequency of the AC pulse signal, and, for example, the frequency of the high-frequency signal may be about 10 times of the frequency of the AC pulse signal. Further, the amplitude of the high-frequency signal may be smaller than the amplitude of the AC pulse signal, and for example, greater than or equal to 1/10 and less than 1. Specifically, an amplitude value E2 of the high-frequency signal illustrated in FIG. 5-(B) with respect to an amplitude value E1 of the AC pulse signal illustrated in FIG. 5-(A) is set about $E2=0.125\times E1$, for example.

The amplitude value E1 of the AC pulse signal, the amplitude value E2 of the high-frequency signal, and the constant value to be multiplied ("0.125" for the above case) may be appropriately adjusted based on ionic characteristics of the skin lotion, condition of the skin to which the iontophoresis is performed or the like.

The wave form for iontophoresis of the embodiment illustrated in FIG. 4-(A) is generated by superimposing the AC pulse signal illustrated in FIG. 5-(A) and the high-frequency signal illustrated in FIG. 5-(B). The file of the signal for iontophoresis in which the wave form for iontophoresis is stored may be installed in the data processing apparatus 20 using the communication network. Alternatively, the file of the signal for iontophoresis may be stored in a storage medium such as a CD-ROM or the like, and may be installed by mounting the storage medium to the data processing apparatus 20.

In this embodiment, by reproducing the file of the signal for iontophoresis installed as such, the wave form for iontophoresis of the embodiment as illustrated in FIG. 4-(A) is obtained. However, alternatively, by providing a first signal generating unit that generates the AC pulse signal illustrated in FIG. 5-(A), a second signal generating unit that generates the high-frequency signal illustrated in FIG. 5-(B), and a signal synthesizing unit that superimposes the signals generated by the signal generating units in the data processing apparatus 20, the wave form for iontophoresis of the embodiment illustrated in FIG. 4-(A) may be generated in the data processing apparatus 20.

Here, the pulse signal is exemplified as the signal wave form for the explanation with reference to FIG. 4, for the explanation purpose. However, the signal wave form of the signal for iontophoresis of the embodiment is not limited to the pulse signal, and the present invention is applicable to other signal wave forms such as a sine wave signal or the like.

By the above configuration, as illustrated in FIG. 4-(A), even when the iontophoresis contribution time period T3 at which the AC pulse signal of the negative (−) polar region is applied is as equal as the iontophoresis contribution time period T2 illustrated in FIG. 4-(C), the high-frequency signal is superimposed at the opposite polar, the positive (+) polar region, as noise, and the AC pulse signal of the opposite polar, positive (+), is canceled or reduced. With this, the movement of the active ingredient toward the opposite side of the inside of the skin can be prohibited and the active ingredient can easily move toward inside of the skin to be impregnated inside of the skin.

In other words, according to the embodiment, even when the high-frequency AC signal such as the audio signal or the like, for example, is output from the general data processing apparatus, by further superimposing a high-frequency signal on the polarity side that does not contribute to the iontophoresis, the movement of the active ingredient toward a direction opposite to the impregnation direction can be suppressed and the impregnation effect of the active ingredient can be increased.

Next, results of an experiment are explained in which the iontophoresis was performed using the above described cosmetic device 10 and the iontophoresis effect was measured after the iontophoresis.

In this experiment, 4MSK (potassium 4-methoxysalicylate: 1%, pH6, that is a derivative of salicylate), that has functions of suppressing generation of melanin and eliminating melanin, was used as the chemical agent of the iontophoresis, and the chemical agent was impregnated in the mask 32. Further, the iontophoresis was performed on a face of each of four panels (subjects).

Further, for the method of applying the signal for iontophoresis to the skin 40, the electrode pad 31 (see FIG. 1) was mounted on the mask 32 that was mounted on the face of each of the panels, and the signal for iontophoresis of the embodiment was provided to the carbon sheet electrodes 33A and 33B via the output terminal 20A and the audio cable 34 from the data processing apparatus 20.

Here, as a reference example, an experiment was also conducted in which the mask 32, in which the chemical agent was impregnated, was mounted on the face of each of the panels, without performing the iontophoresis, and the chemical agent was impregnated in the skin only by this.

Figure 6:
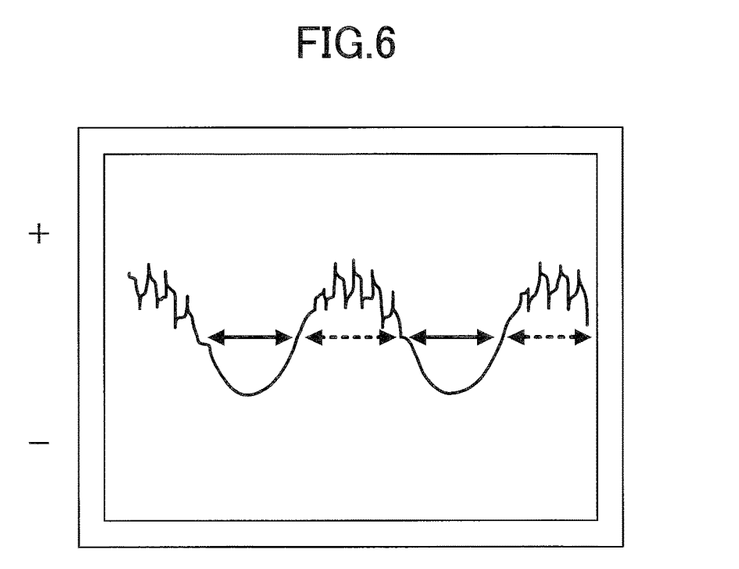
FIG. 6 is a view illustrating a wave form that is an example of the signal for iontophoresis.

FIG. 6 illustrates the signal for iontophoresis of the embodiment used in this experiment. For the iontophoresis signal illustrated in FIG. 6, a sine wave form signal with a frequency f range of 1 Hz<f≤20,000 Hz was used as the AC signal, and a high-frequency signal whose frequency is higher than that of the AC signal was superimposed on the polar region (the region illustrated by a dotted arrows in the drawing) that does not contribute to the iontophoresis. Specifically, for the signal for iontophoresis illustrated in FIG. 6, the frequency of the AC signal was 100 Hz and the frequency of the high-frequency signal was 1000 Hz.

Further, for the data processing apparatus 20 that provides the above described signal for iontophoresis to the cosmetic treatment device 30, an iPhone (registered trademark) was used and the cosmetic treatment device 30 was connected to an output terminal of the iPhone. Further, an iontophoresis portion was a face of a human, and the voltage applied to the carbon sheet electrodes 33A and 33B was ±1.5 V (3 Vpp).

Further, in this experiment, the polarity on which the high-frequency signal is superimposed is switched every 50 seconds. With this, when the high-frequency signal is superimposed on the positive polarity side, negative ions are promoted to be impregnated from the one of the electrodes (carbon sheet electrode 33A, for example), and on the other hand, when the high-frequency signal is superimposed on the negative polarity side, negative ions are promoted to be impregnated from the other of the electrodes (carbon sheet electrode 33B, for example). As such, by switching the polarities, the impregnation promotion effect from the two electrodes 33A and 33B can be obtained.

On the other hand, the iontophoresis effect after the iontophoresis treatment was evaluated as follows. First, a portion where the iontophoresis treatment was performed was washed with a soap, and subsequently, an ion extraction process (a process to extract the chemical agent again after the iontophoresis treatment) was performed on the iontophoresis portion. The ion extraction process is an opposite process of the iontophoresis, and is a process to extract the ions introduced in the skin 40 from the skin 40 by applying an electric potential with a polarity opposite from the ions introduced in the skin 40.

Figure 7:
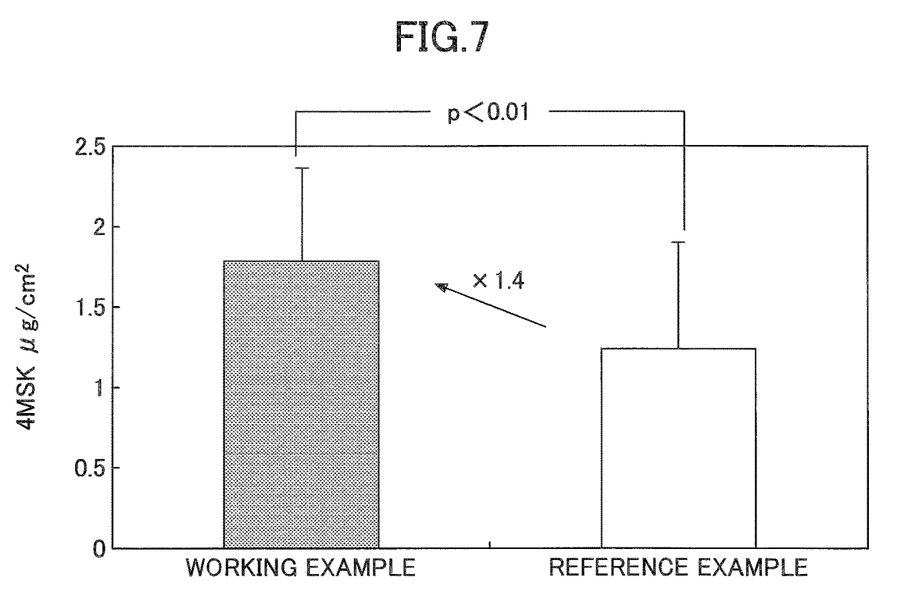
FIG. 7 is a view illustrating an effect that can be obtained when performing the iontophoresis by the signal for iontophoresis.

Then, mass spectrometry was performed on the chemical agent extracted from the iontophoresis portion as such using a liquid chromatography-mass spectrometry. FIG. 7 illustrates the result.

FIG. 7 illustrates average values of the four panels for each of the experimental results. The dotted pattern in the drawing indicates the result in which the iontophoresis was performed using the iontophoresis signal including the high-frequency signal of the embodiment, and the ions were extracted (indicated as a working example). On the other hand, the white indicates the result in which the mask in which the chemical agent was impregnated was just adhered, without performing the iontophoresis, and the ions were extracted thereafter (indicated as a reference example).

The amount of the chemical agent obtained by extracting the ions after performing the iontophoresis using the iontophoresis signal including the high-frequency signal was greater than the amount of the chemical agent obtained by extracting the ions when the chemical agent was adhered without performing the iontophoresis ($p<0.01$, paired-t-test). Specifically, the impregnation effect was improved about 1.4 times for the case using the iontophoresis signal including the high-frequency signal compared with the case without performing the iontophoresis.

Thus, from the experimental result illustrated in FIG. 7, it was demonstrated that the impregnation effect by the iontophoresis was improved by superimposing the high-frequency signal whose frequency is higher than that of the AC signal on the polar region of the AC signal that does not contribute to the iontophoresis even when the AC signal whose frequency f is within a range of 1 Hz<f≤20,000 Hz was used for the signal for iontophoresis.

Although a preferred embodiment has been specifically illustrated and described, it is to be understood that minor modifications may be made therein without departing from the spirit and scope of the invention as defined by the claims.

Although an example was explained in the above embodiment in which the AC signal whose frequency f is within a range of 1 Hz<f≤20,000 Hz is used, the frequency of the AC signal may be less than or equal to 1 Hz. Even when the frequency of the AC signal is less than or equal to 1 Hz, by superimposing the high-frequency signal, that is a noise signal, on the polar region of the signal for iontophoresis that does not contribute to the iontophoresis, the impregnation effect of the active ingredient can be increased.

The present application is based on and claims the benefit of priority of Japanese Priority Application No. 2012-223698 filed on Oct. 5, 2012, the entire contents of which are hereby incorporated by reference.

NUMERALS 10 cosmetic device
20 data processing unit
20A output terminal
30 cosmetic treatment unit
31 electrode pad
32 mask
33 carbon sheet electrode
34 audio cable
40 skin
41 input unit
42 output unit
43 storing unit
44 signal reproducing unit
45 image generating unit
46 network connecting unit
47 control unit
51 input device
52 output device
53 drive device
54 auxiliary storage
55 memory device
56 CPU
57 network connecting device
58 storage medium

What is claimed is:

1. A cosmetic device for performing iontophoresis on the skin of a human, comprising:
an electrode to be mounted on the skin of the human; and
an electric signal providing unit that provides an electric signal to the electrode,
the electric signal being obtained by superimposing an AC signal and a high-frequency signal that has a frequency higher than a frequency of the AC signal,
one of polar regions of the AC signal contributing to the iontophoresis while the other of the polar regions of the AC signal not contributing to the iontophoresis,
the high-frequency signal selectively being superimposed only at the other of the polar regions of the AC signal that does not contribute to the iontophoresis.

2. The cosmetic device according to claim 1,
wherein the frequency f of the AC signal is within a range of $1\ Hz<f\leq 20{,}000\ Hz$.

3. The cosmetic device according to claim 1,
wherein the electric signal providing unit provides the electric signal to the electrode via at least one terminal selected from an earphone terminal, a Dock terminal and a USB terminal.

4. The cosmetic device according to claim 1,
wherein the electric signal providing unit is included in a general data processing apparatus that includes at least one terminal selected from an earphone terminal, a Dock terminal and a USB terminal.

5. The cosmetic device according to claim 1,
wherein the electric signal providing unit is included in a general data processing apparatus including an earphone terminal, and
wherein the electric signal is an audio signal.

6. The cosmetic device according to claim 1,
wherein the high-frequency signal is a noise signal that is selectively superimposed only at a polar region of the AC signal that does not contribute to the iontophoresis.

7. A method of applying a current for performing iontophoresis on the skin of a human, comprising:
providing an electric signal to an electrode that is to be mounted on the skin of the human,
the electric signal being obtained by superimposing an AC signal and a high-frequency signal that has a frequency higher than a frequency of the AC signal,
one of polar regions of the AC signal contributing to the iontophoresis while the other of the polar regions of the AC signal not contributing to the iontophoresis,
the high-frequency signal selectively being superimposed only at the other of the polar regions of the AC signal that does not contribute to the iontophoresis.

8. The method of applying a current according to claim 7,
wherein the frequency f of the AC signal is within a range of $1\ Hz<f\leq 20{,}000\ Hz$.

9. The method of applying a current according to claim 7,
wherein the electric signal is provided from a general data processing apparatus including at least one terminal selected from an earphone terminal, a Dock terminal and a USB terminal.

10. The method of applying a current according to claim 7,
wherein the electric signal is an audio signal that is provided from a general data processing apparatus including an earphone terminal.

11. The method of applying a current according to claim 7,
wherein the high-frequency signal is a noise signal that is superimposed at a polar region of the AC signal that does not contribute to the iontophoresis.

* * * * *